(12) United States Patent
Dixon et al.

(10) Patent No.: US 7,359,545 B2
(45) Date of Patent: Apr. 15, 2008

(54) METHOD AND SYSTEM TO COMPENSATE FOR LAMP INTENSITY DIFFERENCES IN A PHOTOLITHOGRAPHIC INSPECTION TOOL

(75) Inventors: David Dixon, Austin, TX (US); Lloyd Lee, Manchacha, TX (US)

(73) Assignee: Tokyo Electron Limited, Tokyo (JP)

( * ) Notice: Subject to any disclaimer, the term of this patent is extended or adjusted under 35 U.S.C. 154(b) by 841 days.

(21) Appl. No.: 10/749,887

(22) Filed: Dec. 31, 2003

(65) Prior Publication Data
US 2005/0146716 A1    Jul. 7, 2005

(51) Int. Cl.
*G06K 9/00* (2006.01)

(52) U.S. Cl. .................. 382/145; 315/293

(58) Field of Classification Search .......... 382/145, 382/209, 217, 141, 144, 147, 152; 250/559.45; 356/237.4, 237.5; 315/293
See application file for complete search history.

(56) References Cited

U.S. PATENT DOCUMENTS

| | | | | |
|---|---|---|---|---|
| 3,749,496 | A | 7/1973 | Hietanen et al. ............ 356/73 |
| 4,806,776 | A | 2/1989 | Kley ......................... 250/560 |
| 5,039,868 | A | 8/1991 | Kobayashi et al. ......... 250/572 |
| 5,204,910 | A | 4/1993 | Lebeau | |
| 5,335,293 | A | 8/1994 | Vannelli et al. ............. 382/17 |
| 5,581,074 | A | 12/1996 | Yoshida ..................... 250/205 |
| 5,640,237 | A * | 6/1997 | Esrig et al. ............... 356/237.2 |
| 5,835,220 | A | 11/1998 | Kazama et al. ............ 356/369 |
| 5,850,466 | A * | 12/1998 | Schott ........................ 382/141 |
| 5,917,588 | A | 6/1999 | Addiego .................... 356/237 |
| 5,943,437 | A | 8/1999 | Sumie et al. ............... 382/149 |
| 5,995,217 | A | 11/1999 | Watanabe ................... 356/237 |
| 6,064,759 | A | 5/2000 | Buckley et al. ............ 382/154 |
| 6,078,386 | A | 6/2000 | Tsai et al. ................ 356/237.1 |
| 6,151,064 | A | 11/2000 | Connolly et al. ............ 348/93 |
| 6,337,488 | B1 | 1/2002 | Okawauchi ............ 250/559.05 |

(Continued)

FOREIGN PATENT DOCUMENTS

JP     3013850     1/1991

OTHER PUBLICATIONS

Miller, J.G. et al., *Implementing a Fully Automatic Macro Defect Detection and Classification System in a High-Production Semiconductor Fab*, Journal of Microlithography, Macrofabrication, and Microsystems, vol. 2, No. 1, Jan. 2003.

Primary Examiner—Matthew C. Bella
Assistant Examiner—Dennis Rosario
(74) Attorney, Agent, or Firm—Wood, Herron & Evans, L.L.P.

(57) ABSTRACT

An after develop inspection tool considers tool-to-tool variability when determining confidence score for wafers under inspection. A golden wafer is used to calculate a RGB signature as well as the slope of the individual RGB curves for different lamp intensities. These slopes are normalized in order to generate a compensation factor for red values and blue values within a signature. When a wafer is subsequently inspected at an ADI station using a different lamp, the test wafer RGB signature is likely captured at a different lamp intensity. Consequently, when comparing the signatures, the golden wafer RGB signature is adjusted by the compensation factors, based on the different lamp's intensity setting, and this adjusted RGB signature is then used to determine whether a defect exists on the test wafer.

19 Claims, 9 Drawing Sheets

U.S. PATENT DOCUMENTS

| | | | |
|---|---|---|---|
| 6,356,347 B1 | 3/2002 | Watanabe et al. | 356/369 |
| 6,376,852 B2 | 4/2002 | Watanabe et al. | 250/559.22 |
| 6,515,742 B1 | 2/2003 | Ruprecht | 356/237.4 |
| 6,570,650 B1 | 5/2003 | Guan et al. | 356/237.4 |
| 6,784,446 B1* | 8/2004 | Phan et al. | 250/559.4 |
| 7,035,437 B2* | 4/2006 | Yamaguchi | 382/112 |
| 7,043,071 B2* | 5/2006 | Qian et al. | 382/144 |
| 2002/0009220 A1 | 1/2002 | Tanaka | 382/145 |
| 2002/0186368 A1 | 12/2002 | Rosengaus et al. | |
| 2003/0011761 A1 | 1/2003 | Gilat-Bernshtein et al. | 356/237.4 |
| 2003/0059103 A1 | 3/2003 | Shiomi et al. | 382/144 |
| 2003/0081201 A1 | 5/2003 | Shibata et al. | |
| 2003/0086080 A1 | 5/2003 | Guan et al. | 356/237.1 |
| 2004/0052076 A1* | 3/2004 | Mueller et al. | 362/293 |
| 2004/0105093 A1* | 6/2004 | Hamamatsu et al. | 356/237.4 |

* cited by examiner

METHOD AND SYSTEM TO COMPENSATE FOR LAMP INTENSITY DIFFERENCES IN A PHOTOLITHOGRAPHIC INSPECTION TOOL

FIELD OF INVENTION

The following invention relates to inspection equipment in photolithographic environments and, more particularly, to automated control of such equipment.

BACKGROUND

The lithography process for fabricating semiconductor devices can be broken down into three general steps: coating; align/expose, develop. After the develop step is completed, the wafer is inspected for defects which may have occurred in any of the three lithography process areas. Typical defects include problems with photo resist or ARC/BARC coating, edge bead processing, exposure, alignment, development, as well as defects caused by contamination or handling, such as particles or scratches.

Although the chance of misprocessing at any single lithography step is small, a typical wafer goes through 20 to 25 lithography steps. Excursions due to process equipment problems, mishandling, and contamination can occur at each of these steps, so the cumulative probability of a wafer experiencing a yield-limiting defect becomes significant. While most defects impact only a small area of the wafer and do not require rework, some defects impact 30% or more of the wafer. These are defined as global defects. After develop inspection (ADI) procedures detect, classify, and disposition wafers with global lithography defects for rework. Each recovered wafer can result in savings of thousands, or even tens of thousands of dollars, in revenue.

The vast majority of economically re-workable defects are macro-scale, as they are very large relative to the transistors and interconnect structures in the device. Because of their large size, trained operators at microscope stations have traditionally detected macro defects visually. Since manual inspection is a relatively slow process compared to track and stepper throughput, visual inspection has typically been performed on a limited lot-to-lot or within-lot sampling basis. Automating the ADI process for improved throughput has been a challenging problem, as macro defects vary widely in size, type, and appearance, requiring sensitive detection and sophisticated automatic defect classification systems.

In typical systems, after various coating, align/expose, and develop steps, the wafers are delivered to an inspection station that captures a series of whole wafer images using simultaneous dark and bright field illumination. A full-color image of 100% of the wafer is captured and is known as a RGB signature. Such a signature has three elements: a red value, a green value, and a blue value that vary within a predetermined range such as 0-255. The resulting image or signature is compared to that of a "golden" wafer with no defects and a confidence score is assigned indicating how similar the signatures are. When a significant difference is detected, further analysis is performed to classify the defect so that appropriate remedial action can be performed.

One shortcoming of the prior art ADI systems is that they do not account for the tool-to-tool variability in lamp output, or intensity, among the different inspection tools. This variability affects the resulting RGB signature and its values. Thus, a wafer can have a signature that differs from the golden wafer image even if no misprocessing has occurred. This difference between a test wafer's image and the golden wafer image may mistakenly be attributed to a defect even when there is no defect actually present.

Another shortcoming is that when a new ADI tool arrives at a facility its factory settings may vary from the other tools already on the production line and this variance may be significant enough to cause errors when inspecting wafers. Such as, for example, determining that a wafer has a defect when one actually is not present on the wafer.

SUMMARY OF THE INVENTION

Accordingly, embodiments of the present invention relate to an ADI tool and method for its use that considers tool-to-tool lamp variability when evaluating test wafers for defects. The image of a golden wafer is used to calculate a RGB signature at a predetermined lamp intensity as well as the respective slopes of the individual RGB curves for different lamp intensities. These slopes are normalized in order to generate a compensation factor for red values and blue values to apply to a RGB signature. When a wafer is subsequently inspected at an ADI station using a different lamp, the test wafer RGB signature is likely captured at a different lamp intensity. Consequently, when comparing the signatures, the golden wafer RGB signature is adjusted by the compensation factors, based on the different lamp's intensity setting, and this adjusted RGB signature is then used to determine whether a defect exists on the test wafer.

One aspect of the present invention relates to an after develop inspection (ADI) system that includes a first memory and an ADI tool. The first memory stores a first image signature of a golden wafer acquired with a first lamp at a first intensity, and the ADI tool is controllable to capture a second image signature of a test wafer at a second intensity using a second lamp. This system also includes an image signature adjuster, in communication with the first memory, configured to generate an adjusted golden wafer signature by adjusting the first image signature based on a difference between the first intensity and the second intensity. Additionally, a defect analyzer is provided that is in communication with the after develop inspection tool and the image signature adjuster, and is configured to compare the second image signature with the adjusted golden wafer signature.

Another aspect of the present invention relates to a method for inspecting a photolithographically processed wafer. In accordance with this aspect, a first image signature is determined for a golden wafer using a first lamp at a first intensity, and a second image signature is determined for the processed wafer using a second lamp at a second intensity. The first image signature is then adjusted based on a difference between the first intensity and the second intensity to generate an adjusted golden wafer signature. When generating a defect confidence value, the second image signature is compared with the adjusted golden wafer signature instead of the first image signature.

Other embodiments and aspects relate to using similar RGB signature analysis to adjust and calibrate an ADI tool to more closely match other ADI tools on the same production line. Based on golden wafer signature comparisons, the gain levels of a new tool's detectors are adjusted until its RGB signature of the golden wafer matches a known signature. Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

DETAILED DESCRIPTION

During the photo lithography process, a wafer can undergo a variety of coating, exposing and developing steps. Also, throughout the process, a number of different inspection tools can be used at various stages of fabrication to perform ADI or other types of inspection.

Figure 1:
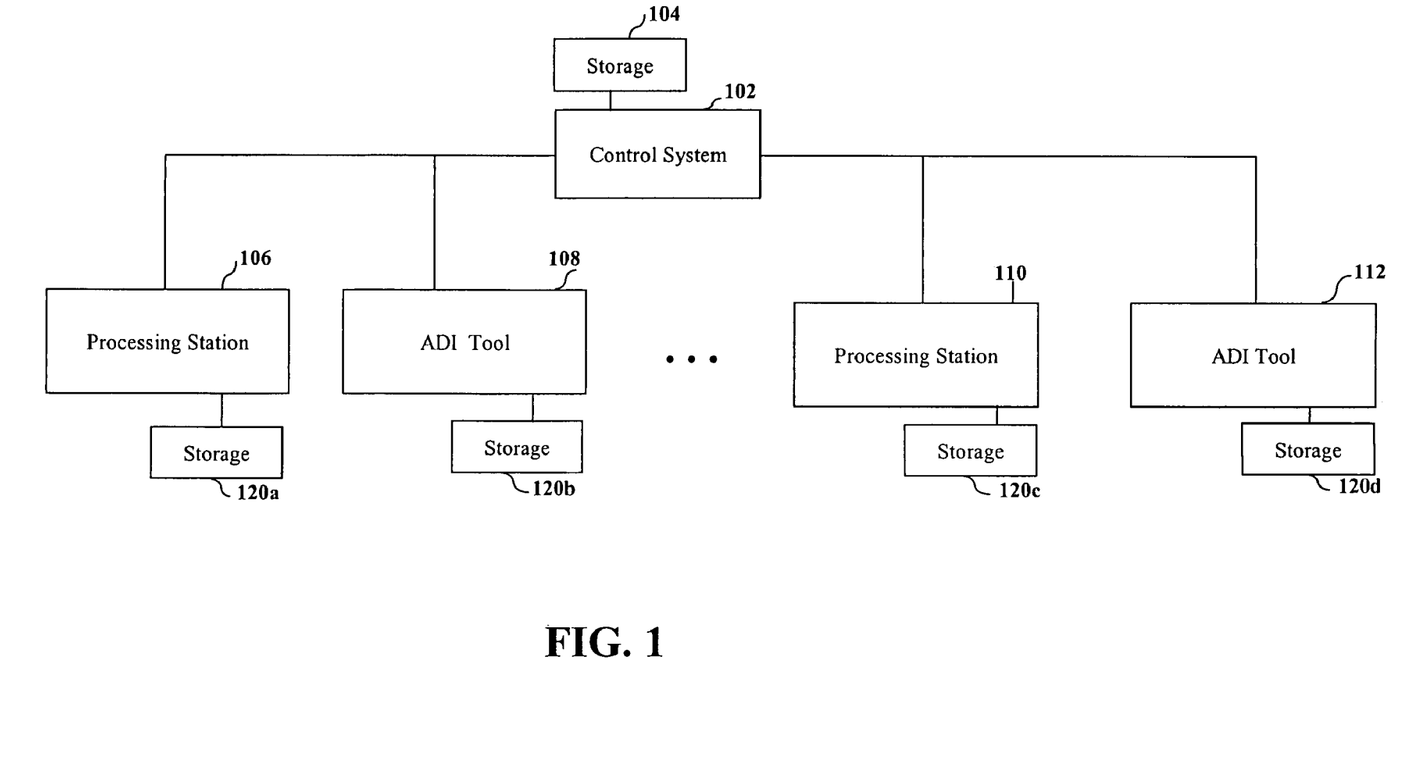
FIG. 1 is a schematic illustration of a photolithographic fabrication environment in which embodiments of the present invention have applicability.

FIG. 1 depicts a schematic view of an automated photo lithography system. In this system, a central control system 102 coordinates the operation of the different processing stations 106, 110 and inspection tools 108, 112. Furthermore, the central control system 102 likely controls the automated transport of wafers between the different stations 106, 108, 110, 112, although such a mechanism is not explicitly depicted in FIG. 1.

The control system 102 can be a programmable computer, or other dedicated microcontroller in communication with each of the process stations 106, 110 and tools 108, 112. When fabricating a wafer, it will run a process recipe and an inspection recipe, each of which specifies the steps and their order necessary to complete the fabrication of the wafer. These recipes can be stored at a central storage 104 of the central control system 102 and can either be executed by the central control system 102 to control a station 106, 110 or tool 108, 112, or can be transmitted to the tool 106, 110 or station 108, 112 for remote execution. Furthermore, the recipes can be distributed to storage 120a-120d locally connected to one of the stations 106, 110 or tools 108, 112.

Each inspection tool 108, 112 has a distinct lamp that illuminates a wafer being inspected. Each lamp has a number of settings that control the apparent brightness, or intensity, produced by the lamp. One way to measure the intensity of a lamp is through the use of a calibration wafer. According to this technique, an image of the calibration wafer is captured at each of the lamp settings. As understood by one of ordinary skill in this field, each such image can be characterized by a RGB signature that varies based on the lamp setting. In particular, the G (green) signature component of each image is used to characterize the lamp intensity at each setting.

Table 1, below, shows a portion of the tabulation of output levels of different tool lamps. This partial table includes, by way of example, G signature values for lamp settings between 34-40. In addition, to these specific intensity values, the tabulation is performed for all the possible settings of each lamp so as to characterize the lamp over its entire range of settings. Such range of useable settings for ADI-related tools typically varies from about 10 through about 60.

TABLE 1

| Lamp Setting | Tool #1 Lamp Output | Tool #2 Lamp Output |
| --- | --- | --- |
| 34 | 116 | 114 |
| 35 | 119 | 117 |
| 36 | 121 | 120 |
| 37 | 123 | 122 |
| 38 | 128 | 127 |
| 39 | 131 | 131 |
| 40 | 133 | 135 |

This table correlating lamp intensity with a lamp setting can be stored at the storage 104 of the central control system 102, at each individual inspection tool, or both. Furthermore, there can be an individual table for each inspection tool, or a consolidated table for a plurality of inspection tools 108, 112 with which the control system 102 communicates.

As mentioned earlier, during device fabrication, a control system 102 automates the process of inspection using what are known as "inspection recipes". These recipes identify, at each inspection tool 108, 112, the proper lamp setting to create a signature to compare with the golden wafer signature. Thus, the proper lamp setting during inspection is based on the intensity at which the golden wafer image was captured. More particularly, an inspection recipe specifies the desired lamp output level, such as the G signature value just described, and the control system 102 automatically controls the inspection tool 108, 112 lamp to select the appropriate lamp setting corresponding to the recipe's specified intensity.

For example, using the above table, a recipe requiring an output value of 125 results in setting 37 on Tool #1 being chosen, resulting in a lamp output of 123. However, if Tool #2 were being used, then setting 38 would be chosen resulting in a lamp output of 127.

Because each lamp's actual output differs from the precise intensity used when capturing the golden wafer image, it induces different tool-to-tool RGB color signatures for the test wafer even if the test wafer is substantially identical to the golden wafer. Thus, a defect may be "found" even if none is present.

Figure 2A:
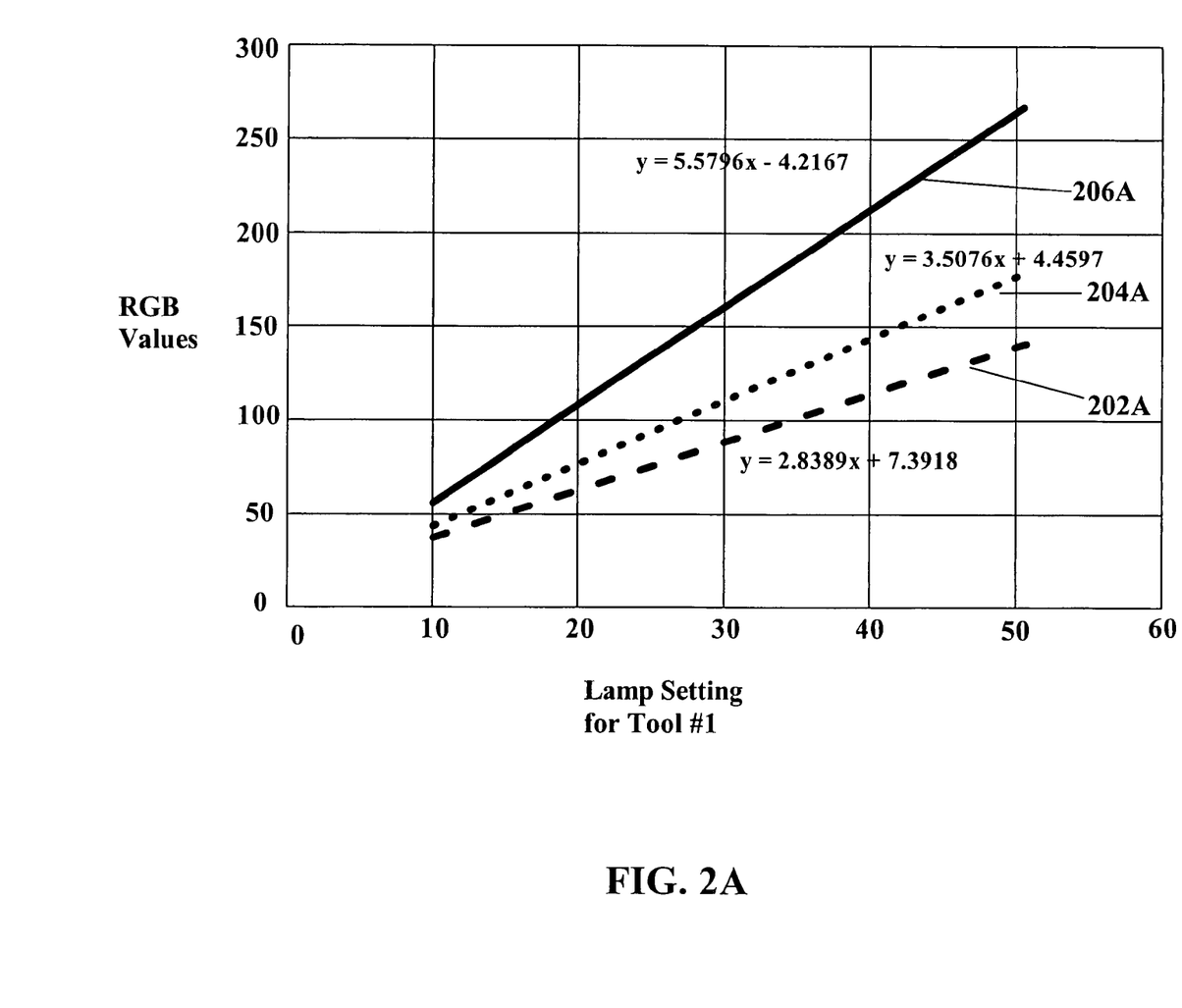
FIGS. 2A-2D are a graphical representation illustrating the effect varying lamp intensity has on the values on a RGB signature for four different tools.

Experiments were performed that calculated the red, green and blue output data versus lamp intensity for each setting for a number of lamps. Thus, as shown in FIG. 2A for the particular lamp of Tool #1, RGB values are plotted over the various lamp settings (ranging from approximately 20-50). Using standard data-fitting techniques, these values can be fitted to a line from which a slope is calculated. In general, as a lamp's intensity setting increases, the values for red, green and blue in the signature increase as well. Because of the variation between the lamps, the resulting plot (see FIGS. 2A-2D) for each tool will be different. For example, as the table above shows, the G output value for setting 37 varies between the two lamps (i.e., 123 vs. 127); similar variance exists over all the lamp setting values as shown by the different plots.

However, by comparing the different plots for a variety of lamps, the experiments showed that certain relationships between the slopes of the individual red, green, blue curves remained substantially similar among the various lamps.

Figure 2B:
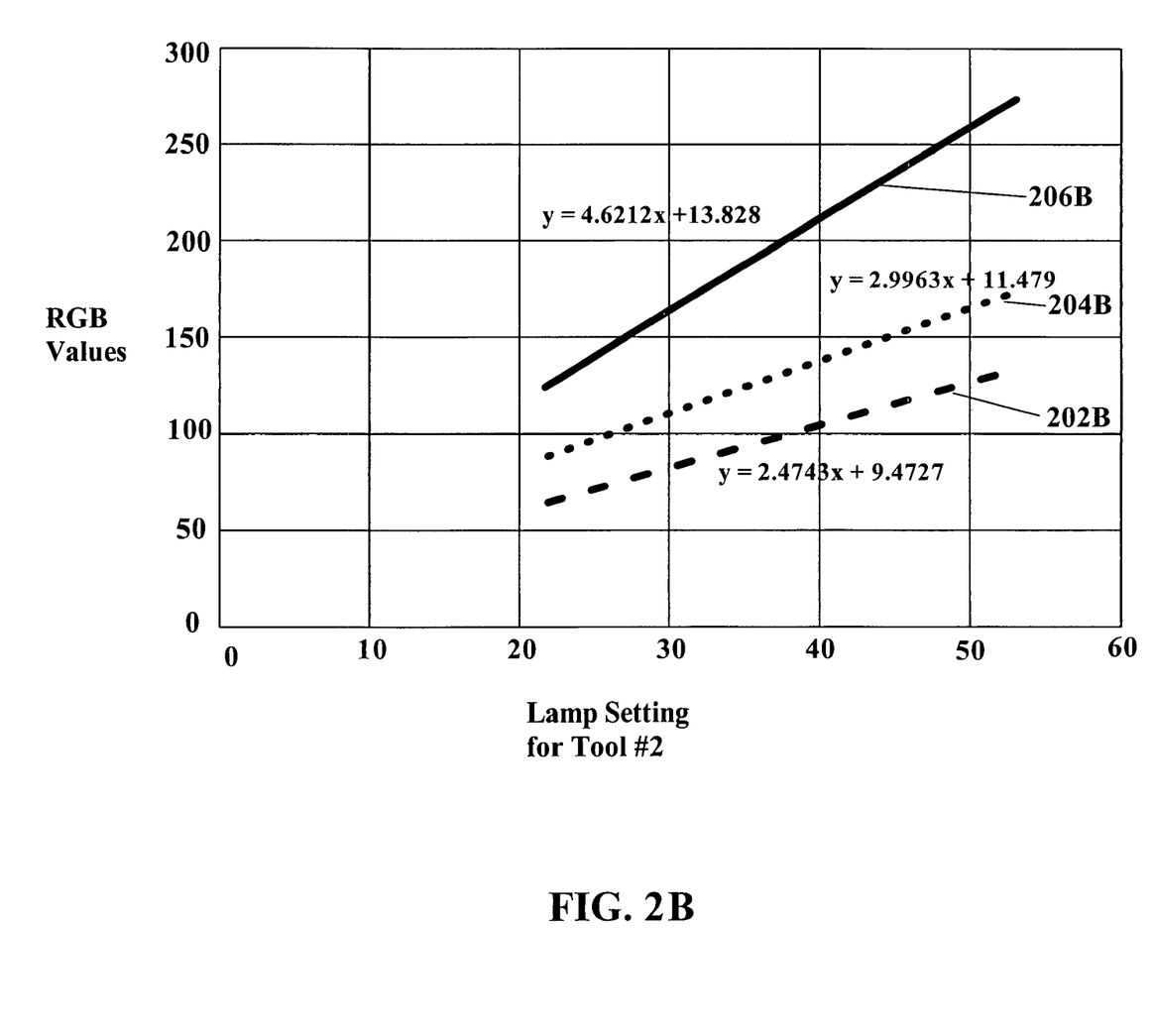
Figure 2C:
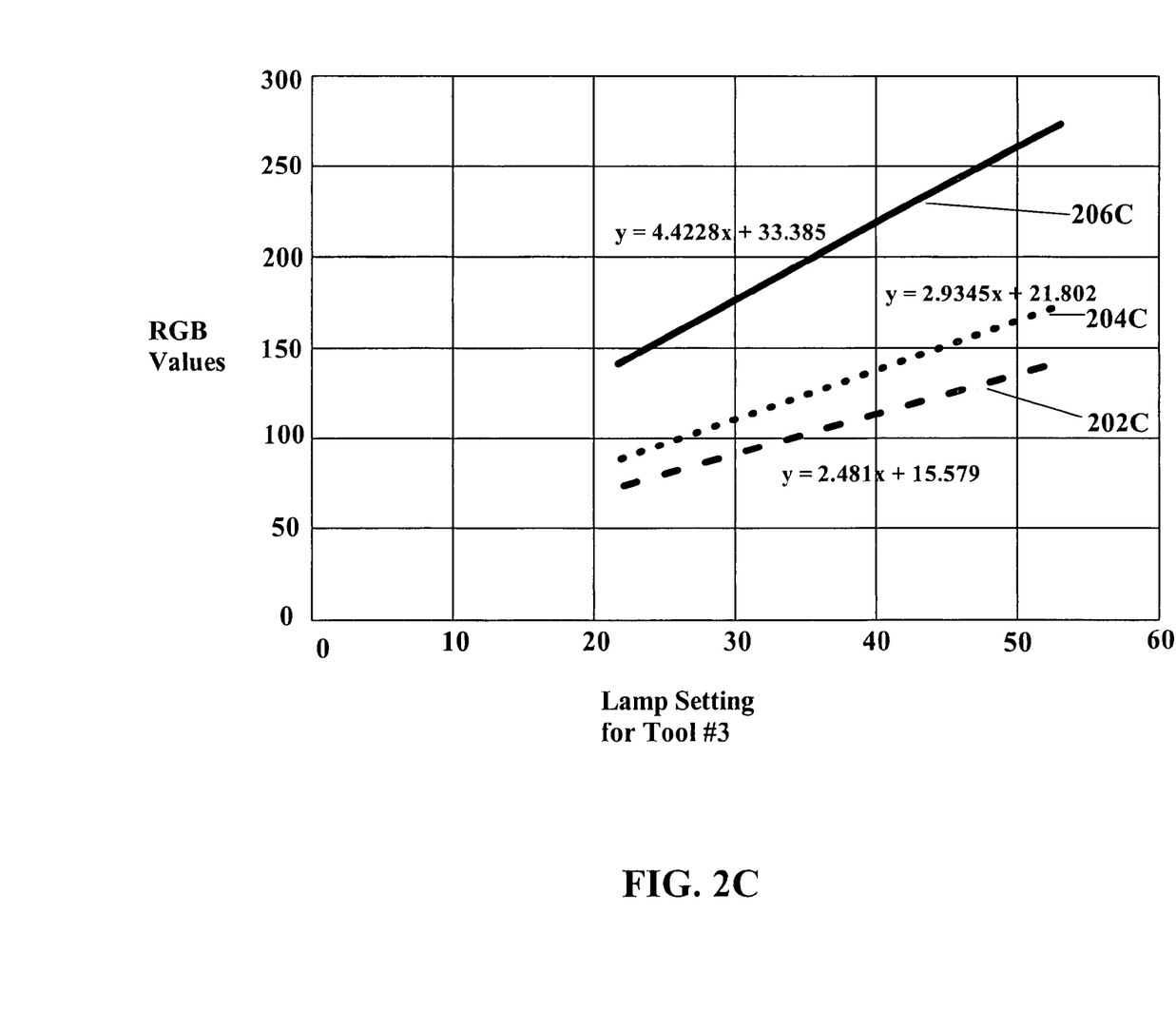
Figure 2D:
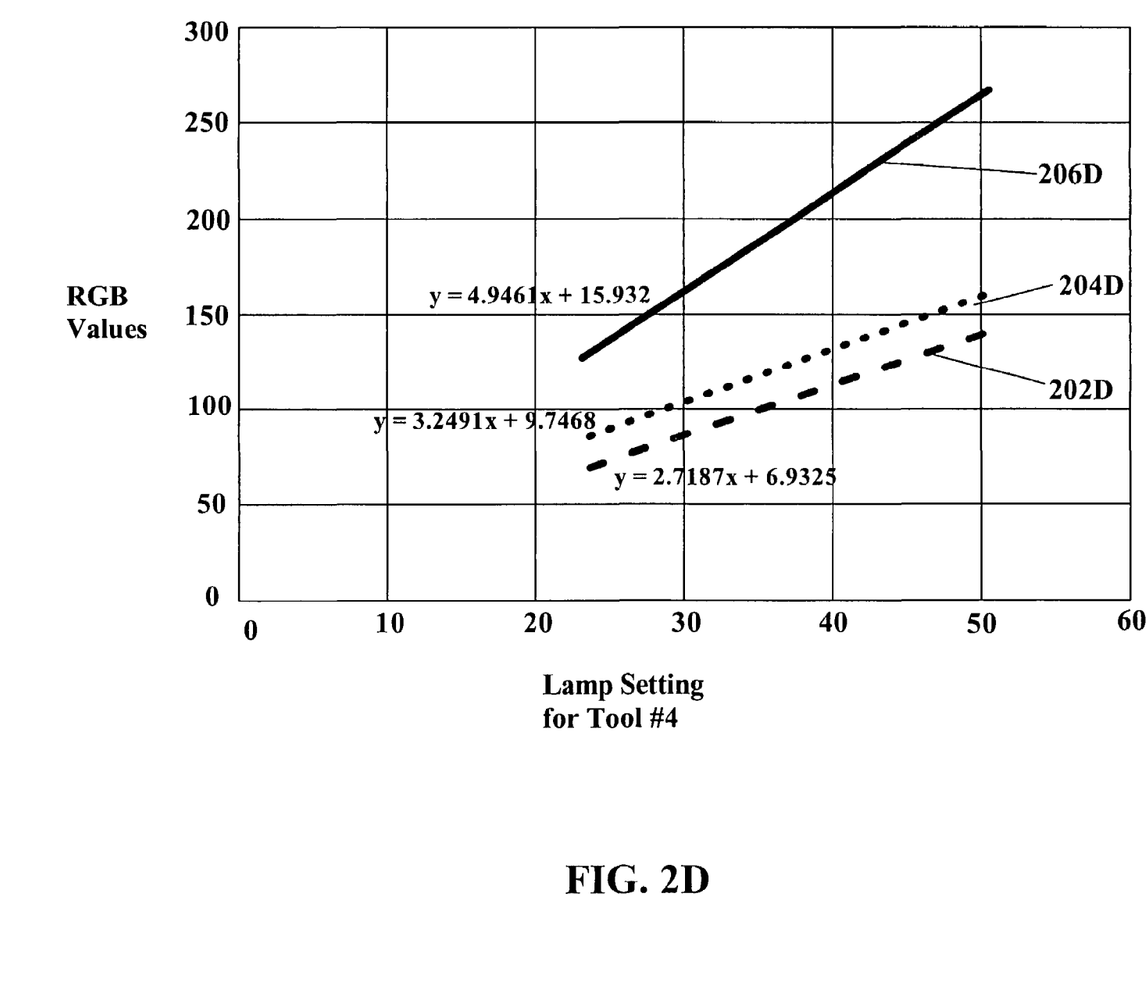

Using for example, the curves of FIG. 2D, the red curve 202D exhibits a slope of approximately 2.7; the green curve 204D exhibits a slope of approximately 3.2; and the blue curve 206D exhibits a slope of approximately 4.9. When these slopes are normalized with respect to the green value, the slopes become 0.8, 1.0 and 1.5, respectively. In other words, these ratios represent the change in one value that accompanies a unit change in the green value, the intensity of the lamp. FIGS. 2A-2C depict blue curves 202A-C, green curves 204A-C, and red curves 206A-C for three different lamps. Across these different lamps, the specific output values changed and even the slopes changed (as expected); however, the ratios between the RGB slopes remained consistently at approximately 0.8, 1.0 and 1.5.

The table below shows exemplary results of tests involving the lamps of four different ADI tools.

TABLE 2

| Tool | Raw Slope | | | Normalized Slope | | |
|---|---|---|---|---|---|---|
| | Red | Green | Blue | Red | Green | Blue |
| #1 | 2.8 | 3.5 | 5.6 | 0.8 | 1.0 | 1.6 |
| #2 | 2.5 | 3 | 4.6 | 0.8 | 1.0 | 1.5 |
| #3 | 2.5 | 2.9 | 4.4 | 0.9 | 1.0 | 1.5 |
| #4 | 2.7 | 3.2 | 4.9 | 0.8 | 1.0 | 1.5 |

These trends held true for a number of different calibration wafers as well.

Figure 3:
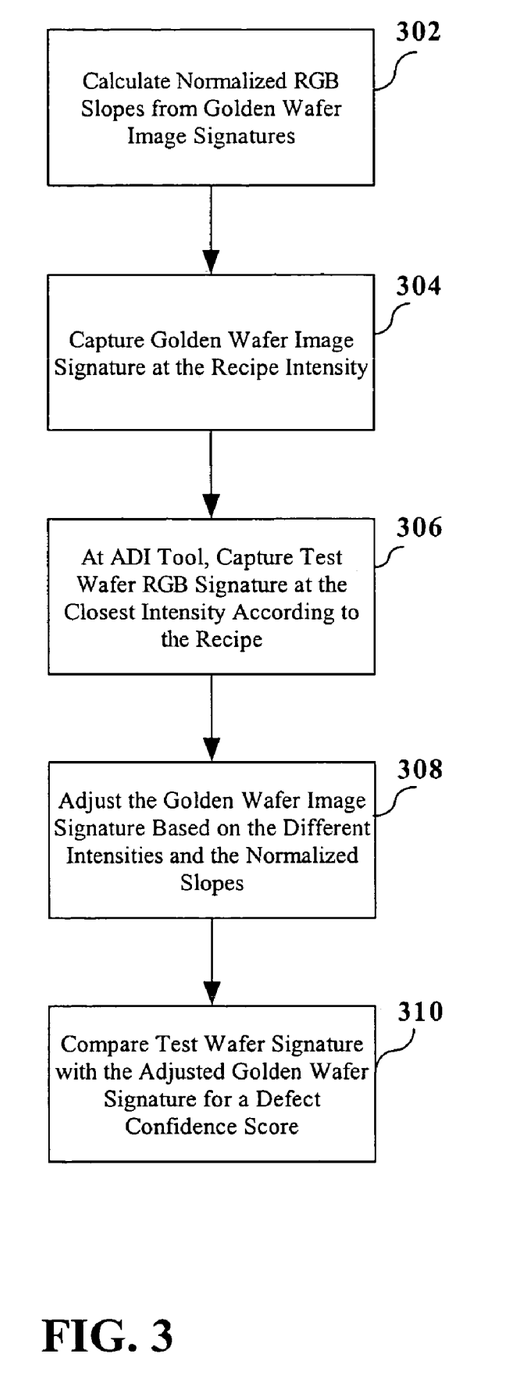
FIG. 3 depicts a flowchart of an exemplary algorithm to account for tool-to-tool lamp variability in an after develop inspection tool according to embodiments of the present invention.

This consistent relationship between the individual RGB curves of different lamps can be utilized to compensate for tool-to-tool variability when applying an inspection recipe at one or more ADI tools. Specifically, the flow chart in FIG. 3 depicts an exemplary algorithm that ADI software on the central control system 102, or distributed among the inspection tools 108, 112, can utilize to compensate for tool-to-tool variability.

In step 302, the software calculates the normalized RGB slopes for the golden wafer. Alternatively, the normalized slopes could be calculated using a calibration wafer instead of the golden wafer. As explained earlier, this would be accomplished by measuring the image signature values, at the golden wafer station, for a number of lamp settings for the individual red, green and blue values, fitting them to a respective line using conventional techniques, and then calculating the slopes and their normalized ratios. From these curves, a normalized slope for the red and blue components can be calculated; thereby indicating how these components of the RGB signature vary according to lamp intensity, or the green value for this lamp. The control system 102 would then store these normalized ratios to be used in later inspection steps.

In step 304, the RGB signature of the golden wafer is captured according to a specific lamp intensity specified in an inspection recipe. Of course, in performing step 302, if the golden wafer is used, the RGB signature of the golden wafer at the recipe's intensity is captured anyway and, therefore, can be utilized without requiring step 304 to be explicitly performed. This RGB signature of the golden wafer is stored by the control system 102 to be used in later inspection steps.

Next, in step 306, the ADI tool 108, 112 is used to test a wafer under production according to the inspection recipe. During this testing, the ADI software selects the closest lamp setting, based on the recipe, and then captures an image of the test wafer at this closest lamp intensity. The RGB signature of the test wafer is then calculated according to conventional methods.

Because the differences in lamp intensity can have an effect on the resulting RGB signature of the test wafer, a compensation step is performed. In particular, in step 308, the ADI software adjusts the RGB signature of the golden wafer according to the normalized ratios calculated in step 302. This adjusting step can be performed by the ADI software by retrieving from storage the normalized slope values and the golden wafer signature. Also, the recipe lamp intensity value and the intensity actually used at the inspection tool would have to be retrieved and compared to calculate a difference. With this difference calculated, the ADI software can easily adjust the RGB signature of the golden wafer accordingly. For each unit of difference in the intensity between the recipe value and the actual inspection value, the red, green and blue values of the golden wafer's RGB signature are adjusted according to the normalized ratios. As just described, the ADI software may implement the image signature adjuster that generates the adjusted golden wafer signature. However, such an adjuster may be implemented as a combination of software and hardware components as well.

It is this adjusted RGB signature that is compared to that of the test wafer, in step 310, when deciding whether a defect exists on the test wafer. Such a defect analyzer of the present invention contemplates utilizing conventional comparison and confidence-scoring techniques to identify the presence of defects as would be known to a skilled artisan. Typically, the respected values of the test wafer are compared to determine if all three are within ±2 of their respective components of the golden wafer signature. Other threshold values can be used as well.

By way of example, assume that the normalized ratios calculated in step 302 are 0.8, 1.0, and 1.5 as shown in Table 2. Furthermore, assume that the inspection recipe specifies that the golden wafer's image signature is R:120, G:125, and B:160. Thus, the recipe specifies that the lamp intensity of the inspection tool should be 125 when inspecting the wafer.

Assuming that the ADI Tool #1 is used (from Table 1), then setting 37 is selected for its lamp setting. At this setting, however, the actual lamp intensity of the ADI tool is 123, not 125. The ADI tool then captures a RGB signature at this intensity setting. However, instead of comparing the test wafer's RGB signature to R:120, G:125, and B:160, the golden wafer signature is adjusted by the ADI software to compensate for tool-to-tool variability.

Specifically, the difference between 125 and 123 is −2. Thus, using the normalized slope ratios, the red value is adjusted by (−2×0.8=−1.6) and the blue value is adjusted by (−2×1.5=−3.0). Also, the green value is adjusted by the difference of −2. Therefore, the RGB signature of the inspected wafer is not compared to the original golden wafer signature; but, instead, is compared to R:118.4, G:123, B:157. From this comparison, the ADI tool generates a confidence score related to whether or not a defect exists on the test wafer.

By comparing the inspected wafer signature and the adjusted golden wafer signature, the ADI software ignores changes in the inspected wafer's RGB signature that are due to differences between the lamps of the ADI tools. Thus, only changes in RGB signatures due to wafer processing differences are considered when determining whether a defect exists on a wafer under inspection.

The previous description focused on compensating for lamp intensity and detector variances within the environment of inspecting processed wafers. However, in addition to such uses, the same principles can be beneficially used to perform tool-to-tool matching for an ADI tool before it is used to inspect processed wafers.

Figure 4:
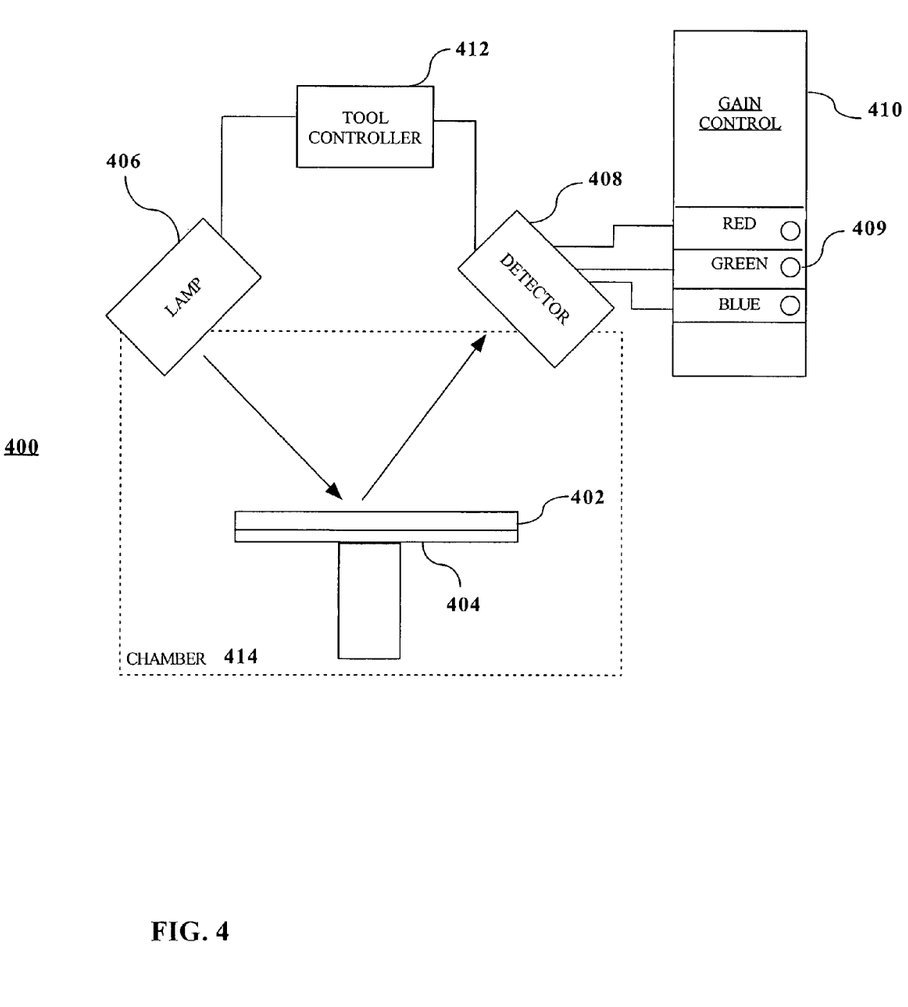
FIG. 4 is a schematic illustration of an after develop inspection tool.

FIG. 4 depicts an exemplary ADI tool 400. Within a protective chamber 414, a wafer 402 is supported on a platform 404 that is often robotically controlled. As explained earlier, the tool 400 is an automated apparatus having a controller 412 that may be a conventional computer or other more-specialized hardware platform.

The controller 412 operates a lamp 406 and a detector 408. In particular, the controller 412 instructs the lamp 406 when to flash and at what intensity. The detector 408, which may be a CCD camera or other similar device, captures an image of the wafer 402 and transmits this image to the controller 412 for further processing.

As is well known to a skilled artisan, the detector 408 includes an adjustable gain level that affects the sensitivity of the detector 408. In a CCD for example, the gain level is used to adjust the count, or units, that is output upon the reception of a certain number of electrons at a pixel. The adjustable gain control 410 is frequently implemented as external knobs or other similar mechanisms 409 accessible from the exterior of the detector 408. More automated detectors or cameras, however, may provide a system interface that can be accessed via a display screen or interface port in order to adjust the gain level via software control. By adjusting the detector gain level, the red, green and blue values generated by the detector for a certain image are adjusted up or down. The detector gain control 410 is advantageously adjustable for each of the red, green, and blue values of the detector 408. Typically, though, the green gain is not adjusted; instead the red and blue detector gain levels are adjusted as needed.

Figure 5:
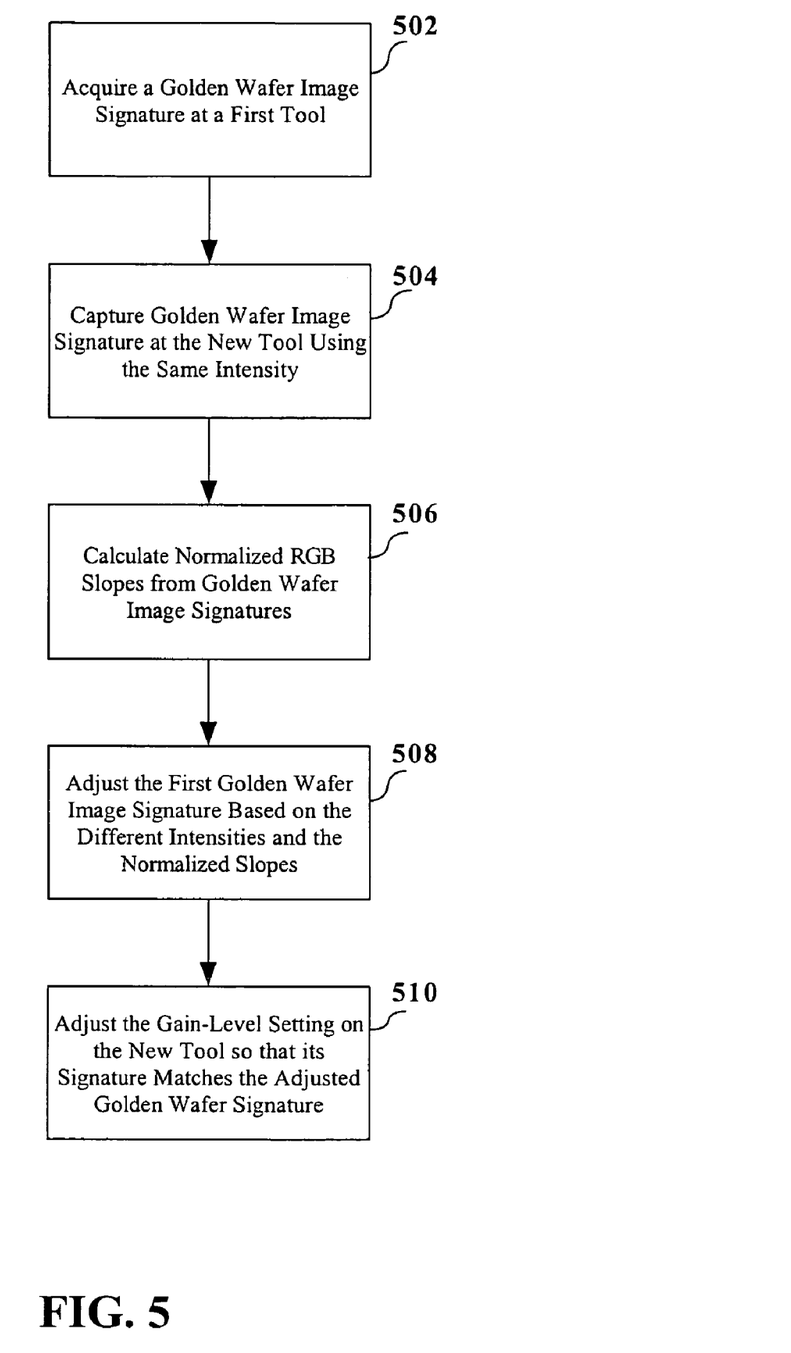
FIG. 5 depicts a flowchart of an exemplary algorithm to account and compensate for tool-tool variability when matching a tool to another tool.

When a new ADI tool is introduced to a production line, matching the ADI tool with other tools already in use may reduce the errors detected by the new tool. FIG. 5 depicts an exemplary algorithm for performing tool-to-tool matching that relies on setting the red and blue detector gain levels to appropriate values.

Using a golden wafer, one tool is used as a reference, in step 502, to generate a RGB signature of the golden wafer. Such as, for example: R=120, G=125, B=160. Frequently, this golden wafer signature has previously been acquired and can be retrieved from an appropriate storage location.

In step 504, the same golden wafer is used at the new tool to capture a RGB signature. Similar to before, the lamp of the new tool is advantageously set to an intensity that is closest to that used for the earlier RGB signature of step 502. The new RGB signature of the golden wafer will likely be different than the earlier one and, for example, may be: R=117, G=123, B=159.

The difference in the two golden wafer signatures are due, in part, to differences in each tool's lamp and detector gain settings. Using the previously discussed methods, a series of images can be generated at different lamp intensity settings in order to calculate, in step 506, the normalized RGB slopes for the lamp of the first, reference ADI tool. If this information has previously been calculated and stored, then it does not need to be re-created but can be retrieved from an appropriate storage location.

In step 508, the normalized slopes are used by an image signature adjuster to adjust the first golden wafer image based on the green intensity of the second, or new, tool. For example, assuming the same normalized ratios as before (i.e., R=0.8, G=1.0, B=1.5), the adjusted first golden wafer signature is calculated to be R=118.4, G=123, B=157. As before, the difference in the two green values is used in conjunction with the normalized slopes to calculate a respective factor by which adjust the red and blue values of the actual RGB signature.

These adjusted values, instead of the original values, are compared with the golden wafer signature from the new tool. Based on this comparison, the gain level control of the new tool is used to adjust the gain level accordingly. For example, at its current red gain level, the new tool detected R=117 instead of 118.4. Thus, the red detector gain control of the new tool is adjusted until the two values correspond. Similarly, the blue detector gain level control is adjusted until the new tool detects a blue value of B=157. The detection of golden wafer images and the resulting gain level adjustments can be iteratively repeated until the two signature values are substantially equal. By this method, the new tool is matched to the first tool.

Figure 6:
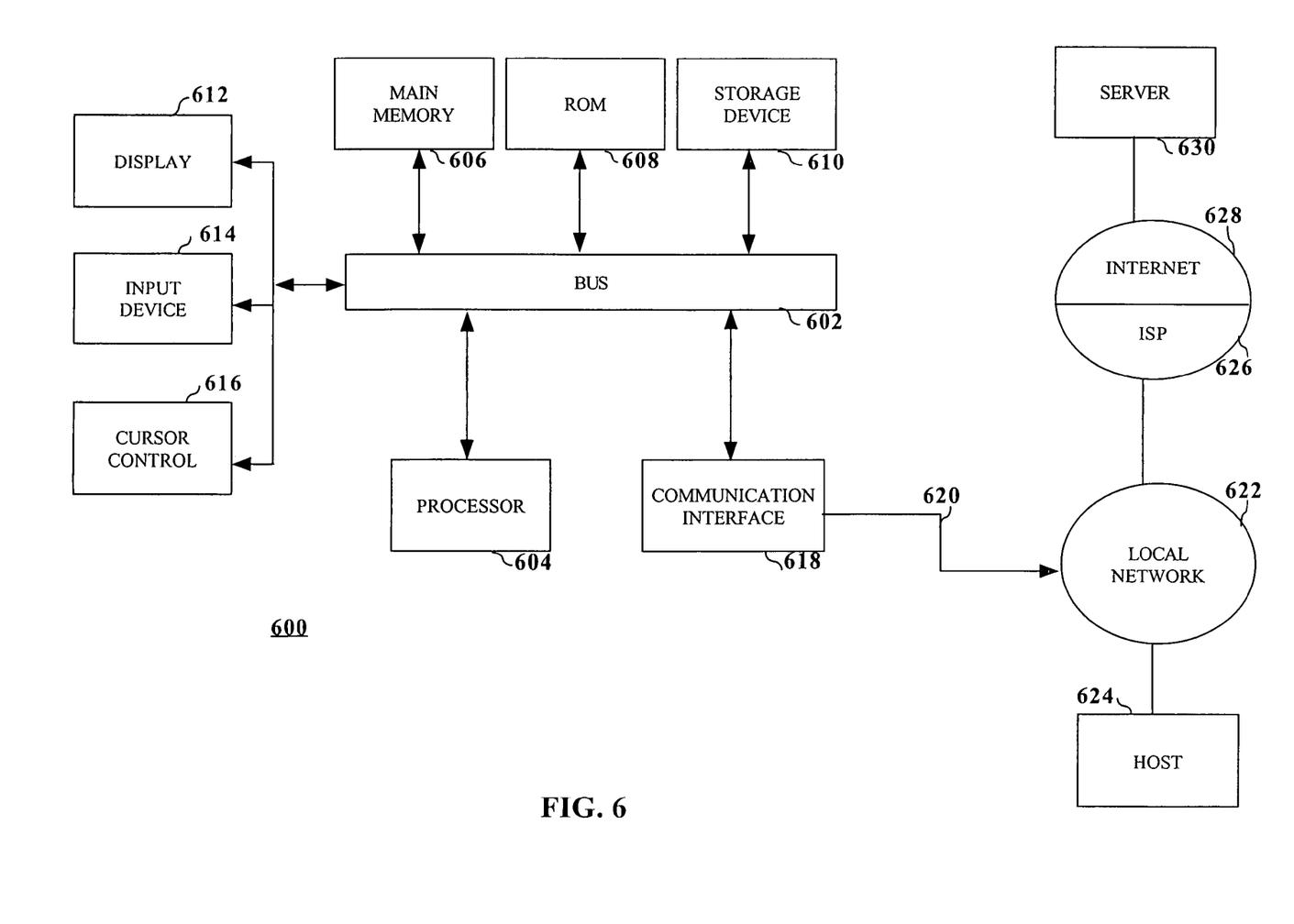
FIG. 6 illustrates an exemplary computer architecture on which embodiments of the present invention may be stored or executed.

The above-described methods for adjusting different image signatures and calculating factors by which to adjust a gain-level setting are advantageously implemented as executable computer code that controls the operation of a microprocessor or computer during execution thereof. This code can be stored on a physical medium such as a disk or tape or can be transmitted signals that travel over various communications media. FIG. 6 provides a general description of a computer system that can execute such code and interface with ADI tools and other photolithography equipment.

Computer system 600 includes a bus 602 or other communication mechanism for communicating information, and a processor 604 coupled with the bus 602 for processing information. Computer system 600 also includes a main memory 606, such as random access memory or other dynamic storage device, coupled to the bus 602 for storing information and instructions to be executed by the processor 604. Main memory 606 also may be used for storing temporary variables or other intermediate information during execution of instructions to be executed by the processor 604. Computer system 600 further includes a read only memory 608 or other static storage device coupled to the bus 602 for storing static information and instruction for the processor 604. A storage device 610, such as a magnetic or optical disk, is provided and coupled to the bus 602 for storing information and instructions.

Computer system 600 may be coupled via the bus 602 to a display 612 for displaying information to a computer user. An input device 614, such as a keyboard, including alphanumeric or other keys, is coupled to the bus 602 for communicating information and command selections to the processor 604. Another type of user input device is a cursor control 616, such as a mouse, a trackball, or cursor direction keys for communicating direction information and command selections to the processor 604 and for controlling cursor movement on the display 612. The computer system 600 operates in response to processor 604 executing one or more sequences of one or more instructions contained in main memory 606. Such instructions may be read into main memory 606 from another computer-readable medium, such as storage device 610. Execution of the sequences of instructions contained in main memory 606 causes processor 604 to perform the process steps described herein. One or more processors in a multi-processing arrangement may also be employed to execute the sequences of instructions contained in main memory 606. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 604 for execution. Such a medium may take many forms, including but not limited to non-volatile media, volatile media, and transmission media. Non-volatile media include, for example, optical or magnetic disks, such as storage device 610. Volatile media include dynamic memory, such as main memory 606. Transmission media include coaxial cables, copper wire, and fiber optics, including the wires that comprise bus 602. Transmission media can also take the form of acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 604 for execution. For example, the instructions may initially be borne on a magnetic disk of a remote computer. The remote computer can load the, instructions into its dynamic memory and send the instructions over a telephone line using a modem. A modem local to computer system 600 can receive the data on the telephone line and use an infrared transmitter to convert the data to an infrared signal. An infrared detector coupled to bus 602 can receive the data carried in the infrared signal and place the data on bus 602. Bus 602 carries the data to main memory 606, from which processor 604 retrieves and executes the instructions. The instructions received by main memory 606 may optionally be stored on storage device 610 either before or after execution by processor 604.

Computer system 600 also includes a communication interface 618 coupled to bus 602. Communication interface 618 provides a two-way data communication coupling to a network link 620 that is connected to a local network 622. For example, communication interface 618 may be an integrated services digital network (ISDN) card or a modem to provide a data communication connection to a corresponding type of telephone line. As another example, communication interface 618 may be a local area network (LAN) card to provide a data communication connection to a compatible LAN. Wireless links may also be implemented. In any such implementation, communication interface 618 sends and receives electrical, electromagnetic or optical signals that carry digital data streams representing various types of information.

Network link 620 typically provides data communication through one or more networks to other data devices. For example, network link 620 may provide a connection through local network 622 to a host computer 624 or to data equipment operated by an Internet Service Provider (ISP) 626. ISP 626 in turn provides data communication services through the world wide packet data communication network, now commonly referred to as the "Internet" 628. Local network 622 and Internet 628 both use electrical, electromagnetic or optical signals that carry digital data streams. The signals through the various networks and the signals on network link 620 and through communication interface 618, which carry the digital data to and from computer system 600, are exemplary forms of carrier waves transporting the information.

Computer system 600 can send messages and receive data, including program code, through the network(s), network link 620, and communication interface 618. In the Internet example, a server 630 might transmit a requested code for an application program through Internet 628, ISP 626, local network 622 and communication interface 618. In accordance with the invention, one such downloaded application provides for hosting distributed objects as described herein. The received code may be executed by processor 604 as it is received, and/or stored in storage device 610, or other non-volatile storage for later execution. In this manner, computer system 600 may obtain application code in the form of a carrier wave.

Although the present invention has been described and illustrated in detail, it is clearly understood that the same is by way of illustration and example only and is not to be taken by way of limitation, the spirit and scope of the present invention being limited by the terms of the appended claims and their equivalents.

The invention claimed is:

1. A method for inspecting a photolithographically processed wafer, comprising the steps of:
   determining a first image signature of a golden wafer using a first lamp at a first intensity;
   determining a second image signature of the processed wafer using a second lamp at a second intensity;
   adjusting the first image signature based on a difference between the first intensity and the second intensity to generate an adjusted golden wafer signature wherein the difference is substantially equal to a respective value of a single color of the second image signature subtracted from a respective value of a single color of the first image signature;
   determining a respective multiple color signature of the golden wafer at each of a plurality of different setting values using the first lamp;
   calculating a color slope corresponding to a change in the respective color values for said single color and a plurality of other colors of said multiple color signature as compared to a change in the setting values;
   normalizing the slopes of each of said other colors with respect to said slope of said single color to generate an adjustment factor for each of said other colors; and
   generating a defect confidence value by comparing the second image signature with the golden wafer signature as adjusted by said adjustment factors.

2. The method according to claim 1, wherein the first image signature and the second image signature are each a RGB signature.

3. The method according to claim 2, wherein each of the first image signature and the second image signature has a respective red value, green value, and blue value.

4. The method according to claim 3, wherein the difference is substantially equal to the respective green value of the second image signature subtracted from the respective green value of the first image signature.

5. The method according to claim 4, further comprising the steps of:
   determining a respective RGB signature of the golden wafer at each of a plurality of different setting values using the first lamp;
   calculating a red slope corresponding to a change in the respective red values as compared to a change in the setting values;

calculating a green slope corresponding to a change in the respective green values as compared to a change in the setting values; and calculating a blue slope corresponding to a change in the respective blue values as compared to a change in the setting values.

6. The method according to claim 1, further comprising the step of:

selecting the second intensity based on an inspection recipe.

7. The method according to claim 6, wherein the inspection recipe identifies the first intensity.

8. A method for inspecting a photolithographically processed wafer, comprising the steps of:

determining a first image signature of a golden wafer using a first lamp at a first intensity;

determining a second image signature of the processed wafer using a second lamp at a second intensity;

adjusting the first image signature based on a difference between the first intensity and the second intensity to generate an adjusted golden wafer signature; and generating a defect confidence value by comparing the second image signature with the adjusted golden wafer signature;

the first image signature and the second image signature each being a RGB signature;

each of the first image signature and the second image signature having a respective red value, green value, and blue value;

the difference being substantially equal to the respective green value of the second image signature subtracted from the respective green value of the first image signature;

determining a respective RGB signature of the golden wafer at each of a plurality of different setting values using the first lamp;

calculating a red slope corresponding to a change in the respective red values as compared to a change in the setting values;

calculating a green slope corresponding to a change in the respective green values as compared to a change in the setting values;

calculating a blue slope corresponding to a change in the respective blue values as compared to a change in the setting values;

normalizing the red slope with respect to the green slope to generate a red adjustment factor; and normalizing the blue slope with respect to the green slope to generate a blue adjustment factor.

9. The method according to claim 8, wherein the step of adjusting further includes the steps of:

adjusting the respective red value of the first image signature based on the difference and the red adjustment factor; and adjusting the respective blue value of the first image signature based on the difference and the blue adjustment factor.

10. A method for inspecting a photolithographically processed wafer, comprising the steps of:

determining a first image signature of a golden wafer using a first lamp at a first intensity;

determining a second image signature of the processed wafer using a second lamp at a second intensity;

adjusting the first image signature based on a difference between the first intensity and the second intensity to generate an adjusted golden wafer signature;

generating a defect confidence value by comparing the second image signature with the adjusted golden wafer signature;

selecting the second intensity based on an inspection recipe wherein the inspection recipe identifies the first intensity; and selecting one of a plurality of different intensity settings for the second lamp that is closest to the first intensity.

11. A method for inspecting a photolithographically processed wafer after a develop step, comprising the steps of:

determining a first RGB signature of a golden wafer using a first lamp at a first intensity;

determining a second RGB signature of the processed wafer using a second lamp at a second intensity;

adjusting the first RGB signature based on a difference between the first intensity and the second intensity to generate an adjusted golden wafer signature; and generating a defect confidence value by comparing the second RGB signature with the adjusted golden wafer signature;

the adjusting step including:

calculating a rate of change in the first RGB signature due to a unit change of lamp intensity; and calculating an amount to adjust the first RGB signature based on the calculated rate of change and the difference between the first intensity and the second intensity.

12. The method according to claim 11, wherein each RGB signature has a respective red value, green value, and blue value.

13. The method according to claim 12, wherein the difference is substantially equal to the respective green value of the second RGB signature subtracted from the respective green value of the first RGB signature.

14. The method according to claim 13, further comprising the steps of:

determining a respective RGB signature of the golden wafer at each of a plurality of different setting values using the first lamp;

calculating a red slope corresponding to a change in the respective red values as compared to a change in the setting values;

calculating a green slope corresponding to a change in the respective green values as compared to a change in the setting values; and calculating a blue slope corresponding to a change in the respective blue values as compared to a change in the setting values.

15. The method according to claim 14, further comprising the steps of:

normalizing the red slope with respect to the green slope to generate a red adjustment factor; and normalizing the blue slope with respect to the green slope to generate a blue adjustment factor.

16. The method according to claim 11, further comprising the step of:

selecting the second intensity based on an inspection recipe.

17. The method according to claim 16, wherein the inspection recipe identifies the first intensity.

18. The method according to claim 17, further comprising the step of:

A method for inspecting a photolithographically processed wafer after a develop step, comprising the steps of:

determining a first RGB signature of a golden wafer using a first lamp at a first intensity;

determining a second RGB signature of the processed wafer using a second lamp at a second intensity;

adjusting the first RGB signature based on a difference between the first intensity and the second intensity to generate an adjusted golden wafer signature; and generating a defect confidence value by comparing the second RGB signature with the adjusted golden wafer signature;

selecting the second intensity based on an inspection recipe, wherein the inspection recipe identifies the first intensity; and selecting one of a plurality of different intensity settings for the second lamp that is closest to the first intensity.

19. A method for inspecting a photolithographically processed wafer after a develop step, comprising the steps of:

determining a first RGB signature of a golden wafer using a first lamp at a first intensity;

determining a second RGB signature of the processed wafer using a second lamp at a second intensity;

adjusting the first RGB signature based on a difference between the first intensity and the second intensity to generate an adjusted golden wafer signature; and generating a defect confidence value by comparing the second RGB signature with the adjusted golden wafer signature;

each RGB signature having a respective red value, green value, and blue value;

the difference being substantially equal to the respective green value of the second RGB signature subtracted from the respective green value of the first RGB signature;

determining a respective RGB signature of the golden wafer at each of a plurality of different setting values using the first lamp;

calculating a red slope corresponding to a change in the respective red values as compared to a change in the setting values;

calculating a green slope corresponding to a change in the respective green values as compared to a change in the setting values;

calculating a blue slope corresponding to a change in the respective blue values as compared to a change in the setting values;

normalizing the red slope with respect to the green slope to generate a red adjustment factor; and normalizing the blue slope with respect to the green slope to generate a blue adjustment factor;

the step of adjusting further including:

adjusting the respective red value of the first RGB signature based on the difference and the red adjustment factor; and adjusting the respective blue value of the first RGB signature based on the difference and the blue adjustment factor.

* * * * *

UNITED STATES PATENT AND TRADEMARK OFFICE
CERTIFICATE OF CORRECTION

PATENT NO. : 7,359,545 B2
APPLICATION NO. : 10/749887
DATED : April 15, 2008
INVENTOR(S) : Dixon et al.

Page 1 of 1

It is certified that error appears in the above-identified patent and that said Letters Patent is hereby corrected as shown below:

In column 3, line 22, "for tool-tool variability" should read --for tool-to-tool variability--.
In column 5, line 40, "for tool-to-fool variability." should read --for tool-to-tool variability.--.
In column 7, line 55, "signatures are due," should read --signatures is due,--.
In column 8, line 5, "which adjust the red and blue" should read --which to adjust the red and blue--.
In column 9, line 29, "computer can load the," should read --computer can load the--.

Signed and Sealed this

Thirtieth Day of June, 2009

JOHN DOLL
*Acting Director of the United States Patent and Trademark Office*